United States Patent [19]

York, Jr.

[11] Patent Number: 4,461,904
[45] Date of Patent: Jul. 24, 1984

[54] 2-(TRISUBSTITUTED PHENYLIMINO)-IMIDAZOLINES

[75] Inventor: Billie M. York, Jr., Forth Worth, Tex.

[73] Assignee: Alcon Laboratories, Inc., Fort Worth, Tex.

[21] Appl. No.: 323,371

[22] Filed: Nov. 20, 1981

[51] Int. Cl.$^3$ .......................................... C07D 233/50
[52] U.S. Cl. ................................................ 548/315
[58] Field of Search ........................................ 548/315

[56] References Cited

U.S. PATENT DOCUMENTS

| 2,938,038 | 5/1980 | Hirt ..................................... 548/315 |
| 3,236,857 | 2/1966 | Zeik et al. ............................ 548/315 |
| 3,468,887 | 9/1969 | Stahle et al. ...................... 548/315 X |
| 3,622,579 | 11/1971 | Stahle et al. ................. 424/273 R X |
| 3,636,219 | 2/1972 | Culik et al. ........................... 424/265 |
| 3,872,121 | 3/1975 | Kummer et al. ............ 424/273 R X |
| 3,931,216 | 1/1976 | Fransmair .......................... 548/315 |
| 4,094,964 | 6/1978 | Jarrott et al. .......................... 424/1 |
| 4,125,620 | 11/1978 | Stahle et al. .................... 424/273 R |
| 4,166,859 | 9/1979 | Stahle et al. .................... 424/273 R |
| 4,213,995 | 7/1980 | Stahle et al. .................... 548/315 X |
| 4,250,186 | 2/1981 | Stahle et al. .................... 424/273 R |
| 4,262,005 | 4/1981 | McCarthy et al. .............. 424/273 R |
| 4,287,201 | 9/1981 | Olson et al. ..................... 424/273 R |
| 4,293,564 | 10/1981 | Stahle et al. .................... 424/273 R |

FOREIGN PATENT DOCUMENTS

| 35393 | 9/1981 | European Pat. Off. ............ 548/315 |
| 43659 | 1/1982 | European Pat. Off. ............ 548/315 |
| 2806811 | 8/1979 | Fed. Rep. of Germany ...... 548/315 |
| 2806775 | 8/1979 | Fed. Rep. of Germany . |
| 2831657 | 2/1980 | Fed. Rep. of Germany ...... 548/351 |
| 2832310 | 2/1980 | Fed. Rep. of Germany ...... 548/347 |
| 2905883 | 8/1980 | Fed. Rep. of Germany . |
| 2947563 | 6/1981 | Fed. Rep. of Germany ...... 548/351 |
| 2949287 | 6/1981 | Fed. Rep. of Germany ...... 548/347 |
| 2950345 | 7/1981 | Fed. Rep. of Germany ...... 548/351 |
| 792696 | 5/1979 | South Africa ...................... 548/315 |
| 1180766 | 2/1970 | United Kingdom ................ 548/315 |
| 1216945 | 12/1970 | United Kingdom ................ 548/315 |
| 1279543 | 6/1972 | United Kingdom ................ 548/351 |
| 1279931 | 6/1972 | United Kingdom ................ 548/351 |
| 1595412 | 8/1981 | United Kingdom ................ 548/315 |

OTHER PUBLICATIONS

DeJonge, A., et al., *Europ. J. Pharm.*, 71 (1981), 411–420.
*Chemical Abstracts*, 96:199688r, (1982), [EP43,659, Beeley, et al., 1/13/82].
Innemee, M., et al., *Naunyn-Schmiedeberg's Arch Pharmacol.*, (1981), 316:294–298.
Depoortere, et al., *Sleep*, (1980), pp. 297–300 (1981).
Cavero, et al., *British Journal of Pharmacology*, 69, 259–296 (1980).
Krieglstein, et al., *Ernst Ophthal.*, 17(2), 149–158 (1978).
DeJonge, et al., *Naunyn-Schmiedegerg's Arch. Pharmacol.*, (1981), 317:8–12.
Arndts, et al., *J. of Pharm. Methods*, 6, 109 (1981).
Rouot, et al., *J. of Labelled Compounds*, (1980), vol. XVII, No. 1, p. 35.
Timmermans, et al., *J. Med. Chem.*, 24, 502 (1981).
DeJonge, et al., *J. Auton. Pharmac.*, 1, 377 (1981).
Leclerc, et al., *Br. J. Pharmac.*, 71, 5 (1980).
Rouot, et al., *C.R. Acad. Sc.* Paris, vol. 286, 909, (1980).
Rouot, et al., *Life Sciences* 25, 769, (1979).
Rouot, B., et al., *Bulletin de la Societe Chimique de France*, (1979), 79, part 2, 520–528.

*Primary Examiner*—Richard A. Schwartz
*Attorney, Agent, or Firm*—Fitch, Even, Tabin & Flannery

[57] ABSTRACT

2-Trisubstituted Phenylimino-imidazolines also known as 2-(trisubstituted anilino)-1,3 diazacyclopentene-(2) compounds and their use for lowering intraocular pressure are disclosed.

10 Claims, No Drawings

2-(TRISUBSTITUTED PHENYLIMINO)-IMIDAZOLINES

This invention relates to new compounds suitable for use in the treatment of glaucoma and ocular hypertension. More particularly, this invention relates to novel 2-(trisubstituted phenylimino)-imidazoline compounds also known as 2-(trisubstituted anilino)-1,3-diazacyclopentene-(2) compounds which exhibit surprising efficacy in the lowering of intraocular pressure (hereinafter "IOP") at dosage levels which do not significantly affect the central nervous system.

In glaucoma and ocular hypertension, the high pressure within the affected eye presses against the blood vessels nourishing the optic nerve head and retina. When these blood vessels collapse under abnormal ocular pressure, an atropy of specific regions of the retina results which ultimately is related to loss of vision and blindness. Heretofore, compounds of this class of α-adrenergics capable of lowering IOP, such as clonidine, also known as 2-(2',6'-dichloroanilino)-1,3-diazacyclopentene-(2) and under the naming and indexing of chemical substances for Chemical Abstracts as 2,6-dichloro-N-(2-imidazolidinylidene)-benzamine, are capable of lowering IOP. However, these compounds affect the central nervous system and lower systemic blood pressure, cause drowsiness and other undesirable side effects. Unexpectedly, it has been discovered that the compounds of the invention exert a selective and local ocular pharmacological action which lowers IOP without lowering systemic blood pressure. When the compounds of the invention are applied topically to the eye they do not have to cross the blood barrier of the brain to effect IOP lowering. These compounds lower IOP through a local or peripheral α-adrenergic action at dose levels which selectively lower IOP without significantly affecting the central nervous system.

The IOP lowering action of the compounds of the invention is unexpected because the locus of action of clonidine type compounds has been deemed in the art to be primarily mediated by the brain. The compounds of the invention surprisingly have been found to be excluded from significant absorption into the central nervous system or brain when administered topically at concentrations capable of lowering ocular IOP. Unexpectedly, therefore, it has been found that the compounds of the invention exert a potent IOP lowering by a local action without significantly lowering systemic blood pressure or causing other central nervous system side effects such as drowsiness.

It has been found that the following novel compounds, and pharmaceutically acceptable free bases and acid salts thereof, will selectively lower IOP at dosage levels which do not lower systemic blood pressure:

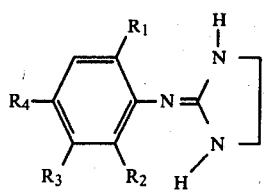

I.

$R_1 = R_2 =$ methyl, ethyl, trifluoromethyl, chloro or bromo, $R_1 \neq R_2 =$ methyl, ethyl, trifluoromethyl, fluoro, chloro or bromo, $R_3$ is selected from

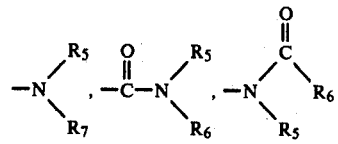

$R_5 =$ H or lower alkyl,
$R_6 =$ H or lower alkyl,
$R_7 =$ H, lower alkyl, 2-hydroxyethyl, 2-hydroxypropyl or 3-hydroxypropyl;
the sum of the carbon atoms in $R_5$ and $R_6$ or $R_5$ and $R_7$ being 4 or less, and $R_4 =$ H; or II.
$R_1 = R_2 =$ ethyl,
$R_3 =$ H,
$R_4 =$

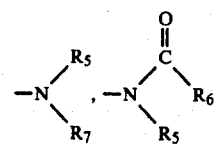

$R_5 =$ H or lower alkyl,
$R_6 =$ H, or lower alkyl,
$R_7 =$ H, lower alkyl, 2-hydroxyethyl, 2-hydroxypropyl or 3-hydroxypropyl.

The alkyl substituents may be straight or branched chain. Generally methyl and ethyl derivatives are preferred because they do not easily enter the central nervous system relative to larger alkyl groups.

The compounds in the form of a salt such as the hydrochloride or dihydrochloride preferably are formulated as aqueous eye drops having a concentration of the compounds of the invention in the range of 0.10 to 2.0 percent by weight. The amount of the eye drops will vary depending upon the concentration of the compounds of the invention. Buffering agents, disinfectants and preservatives may be added as is known in the art.

Examples of the compounds of the invention were made as follows.

EXAMPLE I

N-[3,5-Dichloro-4-(2-imidazolidinylideneamino)-phenyl]-formamide Free Base

N-[3,5-Dichloro-4-(2-imidazolidinylideneamino)-phenyl]-formamide which structurally is

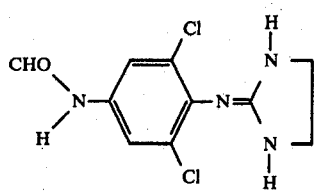

may be made by the following procedure:

Formic acid (35 mL, 98%) and acetic anhydride (15 mL) are stirred and heated at 50° C. for 30 minutes then cooled to 10° C. Then 2,6-dichloro-N¹-(2-imidazolidinylideneamino)-1,4-benzenediamine dihydrochloride (12 g.) are added in portions. The mixture then is heated to 50° C. for 5 hours and then stirred for 6 hours at ambient temperature. Ether (50 ml) is added to the stirred mixture and colorless solids are collected by filtration with ether washes (100 mL) to yield after drying 12.2 g. of product with a melting point of 241°–242° C. with decomposition and a mass spectral analysis of m/e+272 for $C_{10}H_{10}Cl_2N_4O$.

EXAMPLE II 2,6-Diethyl-N-1(2-imidazolidinylidene)-1,4 benzenediamine Dihydrochloride 2,6-Diethyl-N[1]-(2-imidazolidinylidene)-1,4-benzenediamine dihydrochloride which structurally is

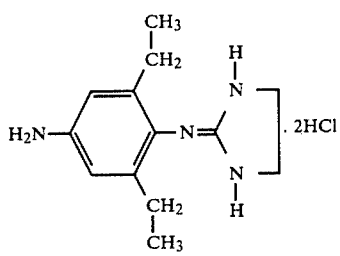

may be made by the following procedure.

1. 1-Acetyl-2-imidazoline may be prepared from 2-imidazoline as follows:

2-Imidazoline (60 g., 0.7 mol) is suspended in acetic anhydride (500 mL) and the mixture is heated to reflux for 30 minutes, then is reduced in volume with heat and reduced pressure to a wet solid. Ethanol (250 mL) is added and a colorless solid collected by filtration. The solid is air dried to yield crude 1-acetyl-2-imidazoline (60.5 g.) having a melting point of 176°–180° C. (literature melting point of 176°–177° C. as reported in *J. Chem. Soc.* 176 (1964).

2. 2,6-Diethyl-N-(2-imidazolidinylidene)-benzamine may be prepared from 1-acetyl-2-imidazoline as follows:

I-Acetyl-2-imidazoline (12.6 g., 0.11 mol) in phosphorus oxychloride (140 mL) is stirred and heated to 45° C., then 2,5-diethylbenzamine (16.5 mL, 0.10 mol) is added at a rate to maintain 50° C. After 24 hours the phosphorus oxychloride is evaporated with heat and reduced pressure. The resultant amber syrup then is poured onto ice (700 cc). The pH is adjusted to 12 with sodium hydroxide, and the aqueous mixture is extracted with methylene chloride (3×75 mL). The combined extracts then are washed with a sodium hydroxide solution (50 mL) and water (2×50 mL) and dried over magnesium sulfate. Evaporation of the methylene chloride results in a solid which is triturated with petroleum ether (30°–60° C. boiling range, 250 mL) and collected by filtration (11.6 g., m.p. 134°–137° C.). Recrystallization from cyclohexane yields 2,6-diethyl-N-(2-imidazolidinylidene)-benzamine, (7.0 g., m.p. 138–139 5° C.). Elemental analysis of the product shows it has the following composition: calculated for $C_{15}H_{21}N_3O$: C 69.46%, H 8.16%, N16.20%; observed C 69.39%, H 8.25%, N 16.27%.

3. 2,6-Diethyl-N-(2-imidazolidinylidene)-benzamine may be prepared from 2,6-diethyl-N-[(1-acetyl-(2-imidazolidinylidene)]-benzamine as follows:

2,6-Diethyl-N-[(1-acetyl-(2-imidazolidinylidene)]-benzamine (4.0 g., 15.4 mmol) is suspended in water (125 mL) and then is heated to reflux. After 3.5 hours the resulting clear colorless solution is cooled, ice is added, and the pH adjusted to 13 with sodium hydroxide. A white precipitate forms and is collected by filtration, is washed with water (80 mL) and then dried to yield 2,6-diethyl-N-(2-imidazolidinylidene)-benzamine free base white powder (3.1 g 93%) with a melting point of 155°–157° C. and a mass spectral analysis of m/e+·217 for $C_{13}H_{19}N_3$.

4. 2,6-Diethyl-4-nitro-N-(2-imidazolidinylidene)-benzamine may be prepared from 2,6-diethyl-N-(2-imidazolidinylidene)-benzamine free base as follows:

2,6-Diethyl-N-(2-imidazolidinylidene)-benzamine (4.35 g., 20 mmol) is added to a solution of fuming nitric acid (4.5 mL) in water at 5° C. Acetic acid (20 mL) then is added to the latter solution. Sodium nitrite (310 mg, 4.5 mmol) then is added to the latter mixture and the reaction is heated to reflux. After two hours, the reaction is cooled to room temperature and additional sodium nitrite (310 mg) in water (4 mL) is added. After four additional hours at reflux the mixture is stirred overnight at room temperature. The reaction mixture is poured onto ice, the pH was adjusted to 13, and a yellow precipitate is collected by filtration and air dried (4.5 g). Column chromatography (silica gel; ethyl acetate, acetone, triethylamine (98:1.5:0.5)) yields 2,6-diethyl-4-nitro-N-(2-imidazolidinylidene)-benzamine which is triturated after drying with petroleum ether, filtered, air dried (0.95 g.) and having a mass spectral analysis of m/e+·262 for $C_{13}H_{18}N_4O_2$.

5. 2,6-diethyl N[1]-(2-imidazolidinylidene)-1,4-benzenediamine dihydrochloride may be prepared from 2,6-diethyl-4-nitro-N-(2-imidazolidinylidene)-benzamine as follows:

2,6-Diethyl-4-nitro-N-(2-imidazolidinylidene)-benzamine (750 mL) is dissolved in ethanol (80 mL). Ethanol washed Raney Nickel (700 mg) then is added and the yellow mixture treated with hydrogen gas (45 psi) overnight to yield a colorless filtrate. The colorless filtrate is evaporated to an oil which forms needles upon standing, the needles having a mass spectral analysis of m/e+·232 for $C_{13}H_{20}N_4$. This solid is then dissolved in methanol (50 mL) cooled to 5° C. and hydrogen chloride gas is bubbled through. After 45 minutes the solution is evaporated to yield an oil which when treated with ethyl ether gives 2,6-(diethyl-N-(2-imidazolidinylidene)-1,4-benzenediamine dihydrochloride which is a colorless powder (0.72 g.) having a melting point with decomposition of 250° C. Elemental analysis for the dihydrochloride salt shows it has the following composition: calculated for $C_{13}H_{22}Cl_2N_4$: C 51.15%, H 7.26%, N 18.35%; observed: C 50.83%, H 7.25%, N 18.09%.

EXAMPLE III

N-[3,5-Diethyl-4-(2-imidazolidinylideneamino)-phenyl]-acetamide Hydrochloride

N-[3,5-Diethyl-4-[(2-imidazolidinylideneamino)-phenyl]-acetamide hydrochloride which structurally is

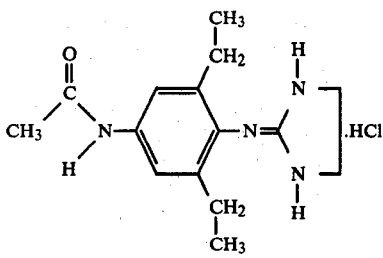

may be made by the following procedure.

2,6-Diethyl-N[1]-(2-imidazolidinylidene)-1,4-benzenediamine dihydrochloride (1.9 g., 6.2 mmol) of Example II is suspended in acetic acid (15 mL) and stirred at room temperature for 20 minutes A solution of acetyl chloride (1.35 mL, 18.6 mmol) in acetic acid (4 mL) is added dropwise to the latter suspension over 15 minutes at ambient temperature. After the addition is complete, the temperature is raised to 50° C. for 5 hours with stirring and then is cooled.

Upon cooling, the reaction mixture is poured onto ice and the pH is adjusted to 13. The resulting solid is extracted into ethyl acetate (100 mL) which is evaporated. The resulting residue is triturated with acetonitrile, is filtered and dried (1.23 g.). The resulting solid is dissolved in chloroform, is treated with charcoal, and filtered through celite. Evaporation of the chloroform under reduced pressure and heat yields a solid form. This solid then is dissolved in methanol and treated with hydrogen chloride gas at 15° C. and after 45 minutes is precipitated with ether. Recrystallization from a methanol and ether combination yields a sample of about 1.1 g. of N-[3,5-diethyl-4-(2-imidazolidinylideneamino)-phenyl]-acetamide hydrochloride having a melting point of 267° C. and a mass spectral analysis of m/e+·274 for $C_{15}H_{22}N_4O$. The isomeric N-[2,4-Diethyl-3-(2-imidazolidinylideneamino)-phenyl]-acetamide may also be prepared.

EXAMPLE IV 3,5-Dichloro-4-(2-imidazolidinylideneamino)-benzenecarboxamide 3,5-Dichloro-4-(2-imidazolidinylideneamino)-benzenecarboxamide which structurally is

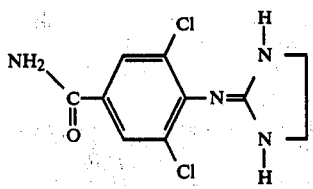

may be made by the following procedures:

Into a three-necked 500 mL round bottomed flask equipped with a mechanical stirrer, reflux condenser, and thermometer and charged with 4-cyano-2,6-dichlorobenzamine (4 g., 0.016 m) in 30 mL of absolute ethanol is added hydrogen peroxide (9 mL of 30% in 81 mL of water) and potassium hydroxide (4.52 g. of 30% solution). The reaction mixture is heated to a temperature of 45° C. over a thirty minute period and maintained at this temperature for two additional hours. At this time, the solution is cooled to 0° C. with an ice bath and filtered to yield 1.8 g. of whitish crystalline material. Subsequent reduction in volume of the filtrate results in an additional 1.1 g. of the same material coming out of solution for a crude yield of 2.9 g. or 68% of theoretical. Recrystallization from water/ethanol solvent leads to a light yellow powder which has a melting point of 243°–245° C. and gives the expected IR with double absorption in the 1700 to 1640 cm$^{-1}$ region.

Elemental analysis for the salt shows it has the following composition: calculated for $C_{10}H_{10}N_4Cl_2$: C 43.98%, H 3.69%, N 20.51%, Cl 25.96%; observed: C 43.82%, H 3.79%, N 20.39%, Cl 26.08%.

Alternatively, this example and other N- and N,N-disubstituted carboxamides can be prepared according to the German Offenlegungsschrift No. 2,905,883, Aug. 28, 1980.

EXAMPLE V 2,6-Diethyl-N[1]-(2-imidazolidinylidene)-1,3-benzenediamine Dihydrochloride 2,6-Diethyl-N[1]-(2-imidazolidinylidene)-1,3-benzenediamine dihydrochloride which structurally is

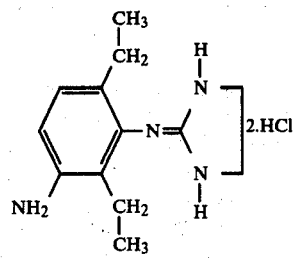

may be made by the following procedure.

1. 2,6-Diethyl-3-nitro-N-(2-imidazolidinylidene)-benezenamine may be prepared from 2,6-diethyl-N-(2-imidazolidinylidene)-benzamine as follows:

Sulfuric acid (20 mL) is cooled to 5° C. and 2,6-diethyl-N-(2-imidazolidinylidene)-benzamine (2.17 g., 10 mmol) is added with rapid stirring. After the solid dissolves to give a dark solution, a mixture of concentrated nitric acid (0.75 mL, 12 mmol) and sulfuric acid (1.0 mL) is slowly added at 0°–5° C. Upon complete addition, the reaction is stirred at 0°–5° C. for one hour and then is poured onto ice (150 mL) and filtered. The filtrate is basified with sodium hydroxide (pH 13) and then is extracted with ethyl acetate (3×100 mL). Chromatography (silica gel; ethylacetate, acetone), triethylamine (92:2.5:0.5) yields a sample (1.5 g.) with a melting point of 131°–133° C. and a mass spectral analysis of m/e+·262 for $C_{13}H_{18}N_4O_2$.

2. 2,6-Diethyl-N[1]-(2-imidazolidinylidene)-1,3-benzenediamine dihydrochloride may be prepared from 2,6-diethyl-3-nitro-N-(2-imidazolidinylidene)-benzamine as follows:

2,6-Diethyl-3-nitro-N-(2-imidazolidinylidene)-benzamine (1g., 3.8 mmol) is dissolved in ethanol (80 mL) and Raney Nickel (1 g.) in ethanol (10 mL) is added. The latter solution then is treated with hydrogen (45 psi) for 15 hours. The resulting almost colorless solution is filtered and evaporated to a foam which then is dissolved in methanol (50 mL), treated with charcoal and filtered. The filtrate is cooled to 5° C. and hydrochloride gas is passed through the solution for ½ hour. The concentrated solution is treated with ethyl acetate and the resulting solid is collected by filtration. Elemental analysis of the salt shows that it has the following composition: calculated for $C_{13}H_{20}N_42HCl$: C 51.15%, H 7.26%, N 18.35%; observed: C 51.06%, H 7.36%, N 18.34%.

EXAMPLE VI 2,6-Dichloro-N¹-(2-imidazolidinylidene)-1,3-benzenediamine Hydrochloride 2,6-Dichloro-N¹-(2-imidazolidinylidene)-1, 3-benzenediamine hydrochloride which structurally is

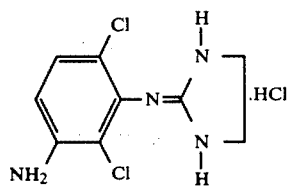

may be made by the following procedure.

1. 2,6-Dichloro-3-nitro-N-(2-imidazolidinylidene)-benzamine is prepared as follows:

2,6-Dichloro-N-(2-imidazolidinylidene)-benzamine or clonidine is prepared according to the procedure of R. Rouot, et al., *J. Med. Chem.*, 19, 1049–54 (1976). Clonidine (11.45 g., 50 mmol) is suspended with stirring in cold sulfuric acid (30 mL). Then a solution of 70% nitric acid (50 mL, 55 mmol) and concentrated sulfuric acid (50 mL) is added dropwise with stirring over a period of thirty minutes. The reaction is stirred for two additional hours at 5°–10° C. and then poured into ice (500 cc) with stirring forming a yellow solution. Sodium hydroxide pellets (28 g.) then are added to the yellow solution. Then 5% sodium hydroxide solution is added to the solution until the pH is approximately 3. Then the pH adjusted solution is extracted with ethyl acetate (5×500 mL). The combined ethyl acetate extracts then are dried over anhydrous sodium sulfate and then are filtered through celite. The filtrate is evaporated with heat and reduced pressure to yield a solid yellow foam which is triturated with hexanes and collected by filtration to yield a product (10.2 g.) with a melting point of 154°–156.5° C. High resolution mass spectroscopy analysis for $C_9H_8Cl_2N_4O_2$: calculated 274.0024, observed 274.0020, error 0.4 mmu/1.5 ppm.

2. 2,6-Dichloro-N¹-(2-imidazolidinylidene)-1,3-benzenediamine hydrochloride may be made from 2,6-dichloronitro-N-(2-imidazolininylidene)-benzamine as follows:

To a mechanically stirred suspension of 2,6-dichloro-3-nitro-N-(2-imidazolidinylidene)-benzamine (5 g., 18 mmol), iron powder (3.1 g., 56 mmol) and ethanol (50 mL) at reflux is added dropwise a solution of concentrated hydrochloric acid (4.6 mL) in 60% ethanol (25 mL). After the addition, the reaction is refluxed for one hour with stirring. Then potassium hydroxide (3N, 17.6 mL) is added while stirring. After the latter addition, the mixture is filtered while hot through a celite pad. The filtrate then is evaporated with heat and reduced pressure. The residue is dissolved in hot methanol treated with activated charcoal and is refiltered through a celite pad. Again the solvent is evaporated leaving an off-white solid (4.1 g.) with a melting point of 263°–266° C. with decomposition. High resolution mass spectroscopy analysis for $C_9H_{10}Cl_2N_4$: calculated 244.0282, observed 244.0291, error 0.9 mmu/3.7 ppm.

The efficacy of several 2-(trisubstituted anilino)-1,3-diazacyclopentene-(2) compounds shown in Table I in lowering IOP without affecting the central nervous system using clonidine as a control was tested by the following biological procedures. (A to E).

A. Rhesus Monkey-Laser Model

Ocular hypertension was produced in adult Rhesus monkeys (4) via an argon laser photocoagulation of trabecular meshwork in the eye. The treated eye (only one is lasered) was allowed to heal and the IOP stabilized after about six weeks. Tests were performed by topical administration of one drop of a 0.5% solution of the test agent to the Ketamine anesthetized Rhesus monkey eye. The IOP charge was recorded by an Alcon Applanation Pneumatonograph. The peak effect was recorded as a percentage change in the hypertensioned eye versus the IOP value of the same eye recorded at the same hour the previous day.

B. Normal Rabbit Model

To determine the IOP reduction efficacy of the anti-glaucoma drugs of the invention in normal albino rabbits the following was done.

New Zealand albino rabbits (12) were acclimatized in restraining boxes for thirty minutes. Alcaine/saline (1:5) was applied to the rabbit eyes and baseline IOP in mm Hg pressure were measured using an Alcon Laboratory applanation phneumatonograph. Then thirty minutes later, the coded test substance versus a coded saline control was administered as a 50 ul drop to one eye, six animals in each group. The treatment effects were measured as a function of time. Mean IOP and mean charge in IOP for each hourly reading was recorded. The effect cited is a peak percentage effect versus the external control test group.

C. The "Steroid" Rabbit Model

Biological procedures for measuring IOP effects of drugs in the "steroid" rabbit model are given in B. L. Bonomi and L. Tomayzol, *Invest. Ophthal.* 15 781 784 (1976) and L. Bonomi et al., *Albrect Graefes Arch. Ophthal.*, 209, 73 89. Luciano Bonomi et al., *Albrect Graefes Arch. Ophthal.*, 219, 1 8, (1979) shows the model works for known anti-glaucoma drugs. In the experiments shown in Table I, a drop of the drug was administered to one eye of the subject rabbit and the IOP in the treated eye was monitored as a function of time.

D. 20% Blood Pressure Decrease In the Rat

Six to eight Sprague-Dawley rats (6 per test group at 200–400 g.) are anesthetized (65 mg/kg sodium pentobarbital) and placed on a heating pad. The femoral artery was cannulated and hydrolically connected to a pressure transducer and Grass Model 7 recorder. A fifteen minute blood pressure reading was recorded. A buffered test agent was given intravenously in a small volume (i.e., 0.1 mL). The test agent effect on blood pressure was then recorded. The mean dose calculated to lower blood pressure 20% in the rat is given in mg/kg.

E. Potentiation of Hexobarbital Induced Anesthesia

Concommitant intraparateneal administration of the test drug and hexobarbital to mice will result in an increase in the duration of anesthesia as compared to hexobarbital alone, if the test compound has sedative activity. This potentiation can be used as a relative measure of central nervous system effect (sedative activity) for comparison of test compounds. The endpoint of anesthesia was recorded as the recovery of the "righting reflex".

TABLE I

| | IOP Lowering Data (Drop in Intraocular Pressure After Topical Administration of Drug) | | | | | |
|---|---|---|---|---|---|---|
| | (A) 50μL 0.5% topical Laser-Monkey % IOP | (B) 50μL 1% topical Normal Rabbit % IOP | (C) 50μL 0.5% topical Steroid Rabbit % IOP | (D) Dose 50 μl/kg 20% b.p. Decease Rat | (E) Dose 50 μl/kg 50% sleeptime pro. in mice tested Na Hexoborbital | (F) IOP[1] hrs. duration |
| $R_1 = R_2 =$ Cl; $R_3 =$ H, $R_4$—NCOH N—[3,5-Dichloro-4-(2-imidazolidinylideneamino)-phenyl]-formamide Free Base | −26.0% | −15.6% | −30.0% | 30.0 | 2,300 | 7–8 |
| $R_1 = R_2 =$ Cl; $R_3 =$ —$NH_2$, $R_4 =$ H 2,6-Dichloro-$N^1$—(2-imidazolidinylidene)-1,3-benzenediamine Hydrochloride | — | 0.0% | −25.0% | 16.0 | 175 | 7 |
| $R_1 = R_2 =$ ethyl; $R_3 =$ H, $R_4 =$ $NH_2$ 2,6-Diethyl-$N^1$—(2-imidazolidinylidene)-1,4-benzenediamine Dihydrochloride | — | — | — | 10.0 | 340 | |
| $R_1 = R_2 =$ ethyl; $R_3 =$ H, $R_4 =$ —NCOCH$_3$ N—[2,6-Diethyl-4-(2-imidazolidinylideneamino)-phenyl]-acetamide Hydrochloride | — | — | — | 130.0 | — | |
| $R_1 = R_2 =$ ethyl; $R_3 =$ —$NH_2$, $R_4 =$ H* 2,6-Diethyl-N'—(2-imidazolidinylidene)-1,3-benzenediamine Dihydrochloride | — | — | — | 100 | 1,100 | |

[1]In testing at present in the steroid rabbit model. Duration if action in the Steroid rabbit model in hours, versus control, statistically significant 95% confidence.

The data in Columns A, B and C of Table I which is expressed as a percent lowering of IOP from control values as well as the data in Columns D, E and F of Table I establishes that the disclosed compounds are capable of lowering IOP at therapeutic levels which do not affect systemic blood pressure or express any overt central nervous system side effects such as sedation.

It should be understood that while certain preferred embodiments of the present invention have been illustrated and described, various modifications thereof will become apparent to those skilled in the art. Accordingly, the scope of the present invention should be defined by the appended claims and equivalents thereof.

Various features of the invention are set forth in the following claims.

What is claimed is:

1. A 2-(trisubstituted phenylimino)-imidazoline compound of the formula or a pharmaceutically acceptable salt thereof:

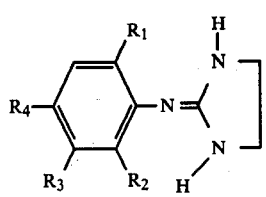

wherein

I.
$R_1 = R_2 =$ methyl, ethyl, trifluoromethyl, chloro or bromo,
$R_1 \neq R_2 =$ methyl, ethyl, trifluoromethyl, fluoro, chloro or bromo,
$R_3$ is selected from

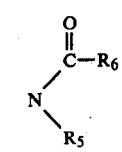

$R_{5'}$ or $R_5 =$ H or lower alkyl,
$R_{6'}$ or $R_6 =$ H or lower alkyl,
but if $R_{6'} =$ methyl then $R_1$ and $R_2$ are not both chloro, the sum of the carbon atoms in $R_5$ and $R_6$ or $R_{5'}$ and $R_{6'}$ being 4 or less, and $R_4 =$ H; or II.
$R_1 = R_2 =$ ethyl
$R_3 =$ H,
$R_4 =$ $$\underset{R_5}{\underset{|}{N}}-\overset{O}{\overset{\|}{C}}-R_6$$

$R_5 =$ H or lower alkyl,
$R_6 =$ H or lower alkyl,
the sum of the carbon atoms in $R_5$ and $R_6$ being 4 or less; or III.
$R_1 = R_2 =$ trifluoromethyl,
$R_1 \neq R_2 =$ methyl, ethyl, trifluoromethyl, fluoro, chloro or bromo and at least one of $R_1$ or $R_2 =$ trifluoromethyl,

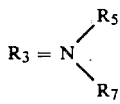

$R_5$=H or lower alkyl, $R_7$=H, lower alkyl, 2-hydroxyethyl, 2-hydroxlpropyl or 3-hydroxylpropyl, the sum of carbon atoms in $R_5$ and $R_7$ being 4 or less, and $R_4$=H; or

IV.

$R_1$=$R_2$=methyl, ethyl, trifluoromethyl, chloro or bromo, $R_1 \neq R_2$=methyl, ethyl, trifluoromethyl, fluoro, chloro, or bromo,

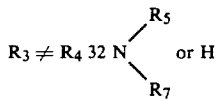

$R_5$=H or lower alkyl $R_7$=2-hydroxyethyl, 2-hydroxylpropyl or 3-hydroxylpropyl, the sum of carbon atoms in $R_5$ and $R_7$ being 4 or less, but if $R_3$=H then $R_1$=$R_2$=ethyl.

2. A 2-(trisubstituted phenylimino) imidazoline compound of the formula or a pharmaceutically acceptable salt thereof:

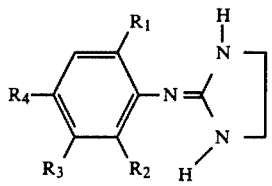

wherein

I.

$R_1$=$R_2$=methyl, ethyl, trifluoromethyl, chloro or bromo, $R_1 \neq R_2$=methyl, ethyl, trifluoromethyl, fluoro, chloro or bromo, $R_3$ is selected from

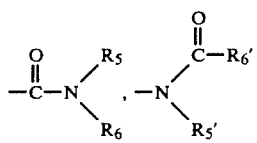

$R_{5'}$ or $R_5$=H or lower alkyl, $R_{6'}$ or $R_6$=H or lower alkyl, but if $R_{6'}$=methyl then $R_1$ and $R_2$ are not both chloro, the sum of the carbon atoms in $R_5$ and $R_6$ or $R_{5'}$ and $R_{6'}$ being 4 or less, and $R_4$=H; or

II.

$R_1$=$R_2$=ethyl $R_3$=H, $R_4$=

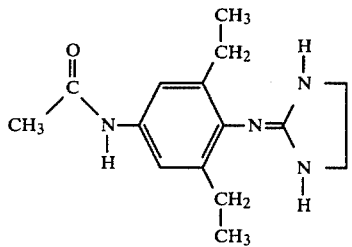

$R_5$=H or lower alkyl, $R_6$=H or lower alkyl, the sum of the carbon atoms in $R_5$ and $R_6$ being 4 or less.

3. A 2-(trisubstituted phenylimino)-imidazoline in accordance with claim 2 having the formula

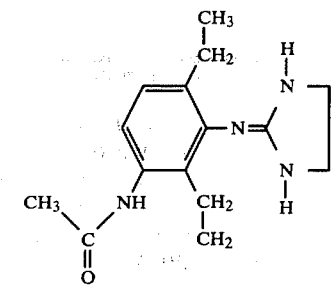

4. A 2-(trisubstituted phenylimino)-imidazoline in accordance with claim 2 having the formula

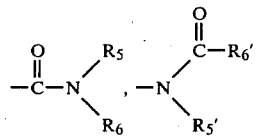

5. A 2-(trisubstituted phenylimino) imidazoline compound as recited in claim 2 wherein in I if $R_{6'}$=lower alkyl, $R_1$ and $R_2$ are each selected from methyl, ethyl or trifluoromethyl.

6. A 2-(trisubstituted phenylimino)-imidazoline compound as recited in claim 2 wherein

I.

$R_1$=$R_2$=methyl, ethyl, trifluoromethyl, chloro or bromo, $R_1 \neq R_2$=methyl, ethyl, trifluoromethyl, fluoro, chloro or bromo, $R_3$ is selected from

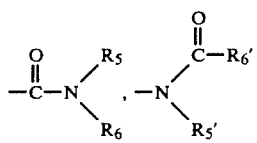

$R_{5'}$ or $R_5$=H or lower alkyl, $R_{6'}$ or $R_6$=H or lower alkyl, but if $R_{6'}$=methyl then $R_1$ and $R_2$ are not both chloro, the sum of the carbon atoms in $R_5$ and $R_6$ or $R_{5'}$ and $R_{6'}$ being 4 or less, and $R_4$=H.

7. A 2-(trisubstituted phenylimino)-imidazoline compound as recited in claim 2 wherein $R_1$=$R_2$=ethyl $R_3 = H$,
$R_4 =$

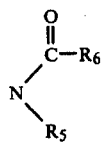

$R_5 =$ H or lower alkyl,
$R_6 =$ H or lower alkyl,
the sum of the carbon atoms in $R_5$ and $R_6$ being 4 or less.

8. A 2-(trisubstituted phenylimino)-imidazoline compound as recited in claim 1 wherein
$R_1 = R_2 =$ methyl, ethyl, trifluoromethyl, chloro or bromo,
$R_1 \neq R_2 =$ methyl, ethyl, trifluoromethyl, fluoro, chloro or bromo,

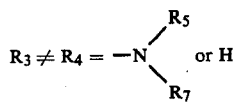

$R_5 =$ H or lower alkyl
$R_7 =$ 2-hydroxylethyl, 2-hydroxylpropyl or 3-hydroxylpropyl,
the sum of carbon atoms in $R_5$ and $R_7$ being 4 or less, but if $R_3 =$ H then $R_1 = R_2 =$ ethyl.

9. A 2-(trisubstituted phenylimino) imidazoline compound of the formula or a pharmaceutically acceptable salt thereof:

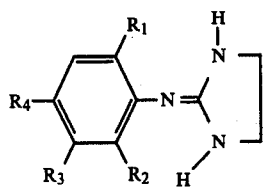

wherein
$R_1 = R_2 =$ ethyl $R_3 = H$,
$R_4 =$

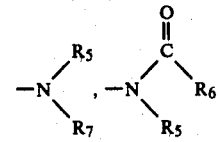

$R_5 =$ H or lower alkyl,
$R_6 =$ H or lower alkyl,
$R_7 =$ 2-hydroxyethyl, 2-hydroxypropyl or 3-hydroxypropyl,
the sum of carbon atoms in $R_5$ and $R_7$ or $R_6$ and $R_5$ being 4 or less.

10. A 2-(trisubstituted phenylimino)-imidazoline compound of the formula or a pharmaceutically acceptable salt thereof:

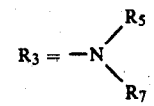

wherein
$R_1 = R_2$ trifluoromethyl,
$R_1 \neq R_2 =$ methyl, ethyl, trifluoromethyl, fluoro, chloro or bromo and at least one of $R_1$ or $R_2 =$ trifluoromethyl, $$R_3 = -N\begin{matrix}R_5\\R_7\end{matrix}$$

$R_5 =$ H or lower alkyl,
$R_7 =$ H, lower alkyl, 2-hydroxyethyl, 2-hydroxylpropyl or 3-hydroxylpropyl,
the sum of carbon atoms in $R_5$ and $R_7$ being 4 or less, and $R_4 =$ H.

* * * * *